United States Patent
Olson et al.

(12)

(10) Patent No.: US 12,044,687 B1
(45) Date of Patent: Jul. 23, 2024

(54) METHOD OF DETECTING CELLULAR REPORTING FOR THERAPY PRODUCTION

(71) Applicant: NantBio, Inc., Culver City, CA (US)

(72) Inventors: Clifford Anders Olson, Culver City, CA (US); Kayyan Niazi, Los Angeles, CA (US); Nicholas J. Witchey, Culver City, CA (US); Wael Tadros, Culver City, CA (US)

(73) Assignee: NantBio, Inc., Culver City, CA (US)

( * ) Notice: Subject to any disclaimer, the term of this patent is extended or adjusted under 35 U.S.C. 154(b) by 671 days.

(21) Appl. No.: 16/818,441

(22) Filed: Mar. 13, 2020

Related U.S. Application Data

(60) Provisional application No. 62/821,117, filed on Mar. 20, 2019.

(51) Int. Cl.

| | |
|---|---|
| *G01N 33/68* | (2006.01) |
| *C12N 5/10* | (2006.01) |
| *C12N 15/10* | (2006.01) |
| *C12Q 1/6897* | (2018.01) |
| *G01N 21/64* | (2006.01) |
| *G01N 33/50* | (2006.01) |

(52) U.S. Cl.
CPC ........... *G01N 33/6872* (2013.01); *C12N 5/10* (2013.01); *C12N 15/1006* (2013.01); *C12Q 1/6897* (2013.01); *G01N 21/64* (2013.01); *G01N 33/5091* (2013.01); *G01N 2333/705* (2013.01)

(58) Field of Classification Search
CPC ...... G01N 33/6872; G01N 21/64; C12N 5/10; C12Q 1/6897
See application file for complete search history.

(56) References Cited

U.S. PATENT DOCUMENTS

| | | | |
|---|---|---|---|
| 7,396,910 B2 | 7/2008 | Bevan et al. | |
| 8,759,091 B2 * | 6/2014 | Tovey | C07K 14/715 435/325 |

FOREIGN PATENT DOCUMENTS

| | | |
|---|---|---|
| WO | 2015/188191 A1 | 12/2015 |
| WO | 2017/066256 A4 | 7/2017 |
| WO | 2017/205810 A8 | 1/2018 |
| WO | 2018/052991 A1 | 3/2018 |
| WO | 2018/089637 A4 | 7/2018 |

OTHER PUBLICATIONS

Weinberg et al., "Large-scale design of robust genetic circuits with multiple inputs and outputs for mammalian cells", Nature Biotechnology, May 2017, vol. 35, No. 5, pp. 12 pages.
Sharif et al., "Cell density regulates cancer metastasis via the Hippo pathway", Future Oncology, 2015, vol. 11, No. 24, pp. 3253-3260.
Bagley et al., "The structural and functional basis of cytokine receptor activation: lessons from the common beta subunit of the granulocyte-macrophage colony-stimulating factor, interleukin-3 (IL-3), and IL-5 receptors", Blood, Mar. 1, 1997, vol. 89, No. 5, pp. 1471-1482.
Palomino et al., "Chemokines and immunity", Einstein, 2015, vol. 13, No. 3, pp. 469-473.
Damaghi et al., "pH sensing and regulation in cancer", Frontiers in Physiology, Dec. 2013, vol. 4, No. 370, pp. 1-10.
Blad et al., "G protein-coupled receptors for energy metabolites as new therapeutic targets", Nature reviews, Drug discovery, vol. 11, Aug. 2012, pp. 603-619.
Yuan et al., "Nutrient sensing, metabolism, and cell growth control", Mol Cell, Feb. 7, 2013, vol. 49, No. 3, 16 pages.
Tkach et al., "Communication by Extracellular Vesicles: Where We Are and Where We Need to Go", Cell, Mar. 10, 2016, vol. 164, pp. 1226-1232.
Ghazarian et al., "A glycobiology review: carbohydrates, lectins and implications in cancer therapeutics", Acta Histochem., May 2011, vol. 113, No. 3, 26 pages.
Manson et al., "Biomarkers associated with checkpoint inhibitors", Annals of Oncology, 2016, 29 pages.
Nishida et al., "Angiogenesis in Cancer", Vascular Health Risk Management , 2006, vol. 2, No. 3, pp. 213-219.
Ward et al., "Biomarkers of apoptosis", British Journal of Cancer, 2008, vol. 99, pp. 841-846.
Milisav Irina, "Cellular Stress Responses (10)", Institute of Pathophysiology, Faculty of Medicine, 2011, pp. 215-232.
Akira et al., "Pathogen recognition and innate immunity", Cell, Feb. 24, 2006, vol. 124, pp. 783-801.
Zhu et al., "How Do Cells Sense Oxygen?", Science, Apr. 20, 2001, vol. 292, No. 5516, 3 pages.
Moqrich et al., "Impaired thermosensation in mice lacking TRPV3, a heat and camphor sensor in the skin", Science, Mar. 4, 2005, vol. 307, pp. 1468-1472.

* cited by examiner

*Primary Examiner* — Gyan Chandra
(74) *Attorney, Agent, or Firm* — Martin Fessenmaier; Umberg Zipser LLP

(57) ABSTRACT

The present disclosure relates to recombinant production reporter cells comprising a logic gate such that an expressible sequence (e.g., a reporter gene) is expressed after the occurrence of triggering event related to a stage of production or an environmental condition of a biological production system. Nucleic acids, kits, and methods for making and using the recombinant production reporter cells are also disclosed herein.

11 Claims, 5 Drawing Sheets

US 12,044,687 B1

METHOD OF DETECTING CELLULAR REPORTING FOR THERAPY PRODUCTION

RELATED APPLICATIONS

This application claims priority to our US provisional patent application with the Ser. No. 62/821,117, which was filed Mar. 20, 2019, and which is incorporated by reference herein.

FIELD OF THE INVENTION

The field of the invention is recombinant reporting cells for sensing a condition or stage of a production, e.g., in an antibody production system, and reporting the stage of production of a biological system such that an expressible sequence (e.g., a reporter gene) is expressed after the condition or stage of production is sensed by the sensor cell.

BACKGROUND

The background description includes information that may be useful in understanding the present invention. It is not an admission that any of the information provided herein is prior art or relevant to the presently claimed invention, or that any publication specifically or implicitly referenced is prior art.

With the advent of personalized therapy for various diseases, the importance of quality control and ascertaining a variety of measures during production of such therapeutics has increased. Many therapeutics are biological products (often referred to as "biopharmaceuticals" or "biologics") that require growth and/or proliferation of living cells for production. The living systems used to produce biologics can be sensitive to very minor changes in the manufacturing process. Small process differences can significantly affect the nature of the finished biologic and, most importantly, the way it functions in the body. To ensure that a manufacturing process remains the same over time, biologics manufacturers must tightly control the source and nature of starting materials, and consistently employ hundreds of process controls that assure predictable manufacturing outcomes.

As many biologics (for example, chimeric antigen receptor (CAR) T cell therapy) move into later-phase clinical trials and become an option for more patients, compliance of the manufacturing processes with global regulatory requirements becomes a topic for extensive discussion. Additionally, the challenges of taking a biologic manufacturing process from a single institution to a large-scale and/or multi-site manufacturing center must be addressed.

Thus, there remains a need for compositions and methods to provide relevant, real time information about biologics production.

SUMMARY OF THE INVENTION

The instant technology generally relates to recombinant production reporter cells comprising an AND gate such that an expressible sequence (e.g., a reporter gene) is expressed after the occurrence of a triggering events. In some embodiments, the recombinant sensor cells comprise a logic gate or circuit (e.g., NOR, OR, XOR, NAND, XNOR, NOT, multiplexer, encoders, decoders, combinations of gates, etc.) where the expression (or repression) of one or more expressible sequences is regulated by the occurrence of a triggering event(s). Nucleic acids, kits, and methods for making and using the recombinant sensor cells are also disclosed.

Weinburg, et al. (Nature Biotechnology 35, pages 453-462 (2017), incorporated herein by reference in its entirety) provides a design for genetic circuits having multiple inputs and outputs in mammalian cells, their design relies on recombinases and is not a reversible system. That is, once the cells containing the genetic circuits are exposed to the recombinase(s), the relevant DNA pieces are excised or inverted, and this cannot be undone rendering such techniques unsuitable for therapeutic uses or biologics manufacturing purposes.

In contrast, the recombinant production reporter cells described herein allow for the reporter to be turned on or off, depending on the microenvironment experienced by the cell at a given time. Thus, the technology described herein provides a dynamic reporter system utilizing genetic circuits to monitor the reporter cell's environment and provide real-time feedback via reporter expression.

The recombinant production reporter cells comprise genetically modified cells comprising logic cassettes, such that the presence or absence of a signal (e.g., from one or more triggering events) results in activation or repression of expression from a reporter gene. In this way, the recombinant production reporter cells identify a set of conditions, for example in a biological production system (e.g., production of a biologic), and report on the presence (or absence) of those conditions. In some embodiments, the production reporter cells sense one or more conditions in the production system, such as a stage of antibody production.

A particular condition, referred to herein as a "triggering event," results in a signal (e.g., presence or binding of a ligand, lack of binding, etc.). The production reporter cell expresses at least one recombinant protein (sensor), which senses a distinct triggering event by binding the signal (e.g., ligand), and is thereby activated by the signal. The activated recombinant protein activates expression of an expressible sequence, such as a reporter, when the condition is present. If one or no recombinant proteins is activated, the expressible sequence is not expressed. This system allows expression of, for example, a reporter protein only when the production reporter cell is in the presence of the signal, e.g., a particular type of cellular microenvironment (e.g., stage of production of a biologic, or a contaminant of the production system).

Alternatively, the production reporter cell may express the expressible sequence, e.g. reporter, and this expression is repressed when a recombinant sensor protein sensor is activated. If one or no recombinant proteins is activated, the expressible sequence is expressed. This system allows expression of, for example, a reporter protein only when the sensor cell is not in the presence of the signal, e.g., a constituent of a particular stage of production of a biologic.

In an aspect, provided herein are methods of detecting at least one constituent in a biological production system. The methods include contacting a sample from the biological production system with a recombinant production reporter cell. The recombinant production reporter cell includes a sensor cassette and a reporter cassette. The sensor cassette includes a first recombinant nucleic acid sequence encoding a sensor protein having a ligand binding portion and an activator portion. The ligand binding portion is capable of binding a ligand from a triggering event related to the at least one constituent. The reporter cassette includes a second recombinant nucleic acid sequence that includes a promoter sequence operably linked to an expressible reporter sequence encoding a reporter protein. Expression from the promoter sequence is activated by the activator portion of the sensor protein, such that the expressible sequence is expressed only after the triggering event occurs. The methods further include detecting the reporter protein, thereby detecting the at least one constituent relative to the sample from the biological production system.

In an aspect, provided herein is a recombinant production reporter cell including a sensor cassette and a reporter cassette. The sensor cassette includes a first recombinant nucleic acid sequence encoding a plurality of sensor proteins, each sensor protein having a ligand binding portion and an activator portion. The ligand binding portion of each distinct sensor protein is capable of binding a distinct ligand from a distinct triggering event. The production reporter cell further includes a reporter cassette comprising a second recombinant nucleic acid sequence comprising a plurality of distinct promoter sequences, each promoter operably linked to a distinct expressible sequence. Expression from each promoter sequence is activated by the activator portion of a respective distinct sensor protein, such that the expressible sequence is expressed only after a distinct triggering event occurs.

In an aspect, provided herein is a kit including a sensor cassette and a reporter cassette. The sensor cassette includes a first recombinant nucleic acid sequence encoding a plurality of sensor proteins, each sensor protein having a ligand binding portion and an activator portion. The ligand binding portion of each distinct sensor protein is capable of binding a distinct ligand from a distinct triggering event. The reporter cassette includes a second recombinant nucleic acid sequence comprising a plurality of distinct promoter sequences, each promoter operably linked to a distinct expressible sequence, where expression from each promoter sequence is activated by the activator portion of a respective distinct sensor protein, such that the expressible sequence is expressed only after a distinct triggering event occurs.

DETAILED DESCRIPTION

Figure 1:
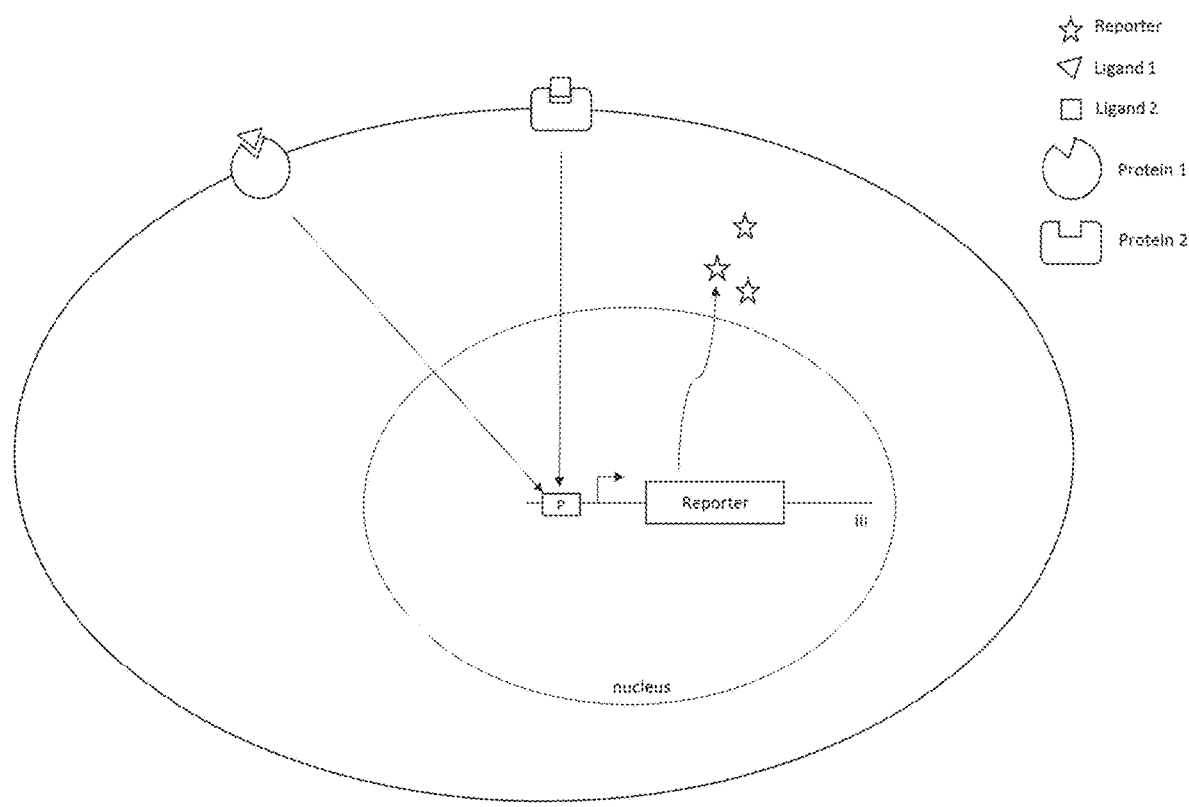
FIG. 1 is a schematic of an example production reporter cell as described herein.

After reading this description, it will become apparent to one skilled in the art how to implement the invention in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth below.

Before the present invention is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description of the invention is divided into various sections only for the reader's convenience and disclosure found in any section may be combined with that in another section. Titles or subtitles may be used in the specification for the convenience of a reader, which are not intended to influence the scope of the present invention.

Definitions

Unless defined otherwise, all technical and scientific terms used herein have the same meaning as commonly understood by one of ordinary skill in the art to which this invention belongs. In this specification and in the claims that follow, reference will be made to a number of terms that shall be defined to have the following meanings:

The terminology used herein is for the purpose of describing particular embodiments only and is not intended to be limiting of the invention. As used herein, the singular forms "a", "an" and "the" are intended to include the plural forms as well, unless the context clearly indicates otherwise.

As used herein, the term "optional" or "optionally" means that the subsequently described event or circumstance can or cannot occur, and that the description includes instances where the event or circumstance occurs and instances where it does not.

As used herein, the term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to a dose amount means that the dose may vary by +/−10%.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this invention.

As used herein, the term "antibody" refers to a polypeptide encoded by an immunoglobulin gene or functional fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

As used herein, the term "biologics" or "biologic drug" refers to a product that is produced from living organisms or contain components of living organisms. Biologic drugs include a wide variety of products derived from human, animal, or microorganisms by using biotechnology. Types of biologic drugs include vaccines, blood, blood components, cells, allergens, genes, tissues, and recombinant proteins. Biologic products may contain proteins that control the action of other proteins and cellular processes, genes that control production of vital proteins, modified human hormones, or cells that produce substances that suppress or activate components of the immune system. Biologic drugs are sometimes referred to as "biologic response modifiers" because they change the manner of operation of natural biologic intracellular and cellular actions.

As used herein, the term "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. The preferred antibodies of, and for use according to the invention include humanized and/or chimeric monoclonal antibodies.

As used herein, the phrase "at least one of A and B" is intended to refer to 'A' and/or 'B', regardless of the nature of 'A' and 'B'. For example, in some embodiments, 'A' may be single distinct species, while in other embodiments 'A' may represent a single species within a genus that is denoted 'A'. Likewise, in some embodiments, 'B' may be single distinct species, while in other embodiments 'B' may represent a single species within a genus that is denoted 'B'.

As used herein, the term "biologic production system" or "biological production system" refers to the manufacturing process by which a biologic or biologic drug is produced. For example, a biologic product system may include a fermenter for growing live cells, a step for harvesting a protein mixture, steps for purification and concentration of the biologic drug and formulation and/or filling steps for a final biological drug product.

As used herein, the term "cell" refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaroytic cells. Prokaryotic cells include but are not limited to bacteria. Eukaryotic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsinization. The term "cell" also may refer to an exosome or enucleated cell that contains sufficient intracellular machinery to carry out transcription and translation.

As used herein, the term "contacting" is used in accordance with its plain ordinary meaning and refers to the process of allowing at least two distinct species (e.g. chemical compounds including biomolecules or cells) to become sufficiently proximal to react, interact or physically touch.

As used herein, the term "expression" includes any step involved in the production of the polypeptide including, but not limited to, transcription, post-transcriptional modification, translation, post-translational modification, and secretion.

As used herein, the term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

Production Reporter Cells

The present disclosure relates to recombinant production reporter cells, and cell lines comprising a plurality of the recombinant production reporter cells. In some embodiments, the recombinant production reporter cell is capable of sensing at least one triggering event, for example a constituent in a biological production system, via recombinant proteins expressed by the cell that bind a ligand or other signal that results from the presence/occurrence of the triggering event. Once the cell senses one or more of the triggering events, an expressible sequence is expressed by the cell. In some embodiments, the expressible sequence encodes a reporter (e.g., mRNA or protein). Thus, presence of the constituent results in a signal from the cell, indicating the presence of the constituent.

The condition or constituent to be sensed may related to a stage of production of a biological production system. In non-limiting examples, the condition or constituent may be related to proper production of a target construct, proper environmental conditions, and/or improper environmental conditions. Specifically, the conditions or constituents may be pH, presence of a particular cytokine, presence of a properly folded antibody, presence of an improperly folded antibody, hypoxia, a contaminant, or a metabolite. Conditions to be sensed may be any combination of two (or more) conditions as disclosed herein. See Table 1 for a non-limiting list of example conditions.

In some embodiments, the signal that results from the presence/occurrence of the triggering event results in ligand binding, phosphorylation, ubiquitination, hydrolysis, nitration, sulfhydration, acetylation, lipid modification, methylation, glycosylation, propionylation, butyrylation, succinylation, malonylation, palmitoylation, and/or crotonylation of the recombinant protein.

In some embodiments, the recombinant production reporter cell includes a first recombinant nucleic acid sequence encoding a plurality of sensor proteins, each sensor protein having a ligand binding portion and an activator portion, where the ligand binding portion of each distinct sensor protein is capable of binding a distinct ligand from a distinct triggering event, and a reporter cassette that includes a second recombinant nucleic acid sequence. The reporter cassette includes a plurality of distinct promoter sequences, each promoter operably linked to a distinct expressible sequence, where expression from each promoter sequence is activated by the activator portion of a respective distinct sensor protein, such that the expressible sequence is expressed only after a distinct triggering event occurs.

Preferably, each of the first and subsequent nucleic acid sequences are recombinant nucleic acid sequences, i.e., they are not endogenous to the cell.

In some embodiments, the activator portion comprises a chromatin remodeler, a histone acetyltransferase, a histone deacetylase, a kinase, a methylase, a transcription factor, or a transcription co-factor.

In some embodiments, the recombinant production reporter cell further comprises at least one additional logic cassette comprising a third nucleic acid sequence. The third nucleic acids includes a second promoter sequence operably linked to a second expressible sequence, where expression from the second promoter sequence is activated by a first activator portion and a second activator portion, such that the second expressible sequence is expressed only after the first and second triggering events occur. In some embodiments, the second expressible sequence encodes a reporter. In some embodiments, the second expressible sequence encodes a therapeutic molecule, a cytotoxic pathway molecule, a pro-apoptotic protein, an immunostimulator, or an immunorepressor. In some embodiments, the expressible sequence and the second expressible sequence are different sequences. Preferably, the protein or mRNA encoded by the second expressible sequence is different from a protein or mRNA encoded by the expressible sequence.

Although many of the sensor/reporter cassettes described herein are AND gates, one of skill in the art would understand that sensor/reporter cassettes comprising other types of logic gates are covered herein. The sensor/reporter cassette may include any type of logic gate or combination of logic gates that are turned on or off by at least two conditions, such as and without limitation, AND, NAND, OR, NOR, XOR, XNOR gates. See, e.g., Weinberg et al. and WO 2015/188191, each of which is incorporated herein by reference in its entirety.

In embodiments, the sensor/reporter cassette comprises a NAND gate. In one embodiment, the recombinant production reporter cell includes a first sensor cassette and a second sensor cassette, such that each sensor cassette is responsive (e.g., transcriptionally, translationally, or activation/repression of the activity of a protein expressed therefrom) to a different triggering event, and a logic cassette that includes a nucleic acid sequence comprising a promoter operably linked to an expressible sequence. In embodiments, the expressible sequence is expressed in the absence of the triggering events and is repressed only when both triggering events occur. For example, the sensor cassettes may express transcriptional repressors or co-repressors in response to the triggering events, and the transcriptional repressors repress the promoter of the logic cassette; the sensor cassettes may express transcriptional activators that are repressed by the triggering events; etc. In one embodiment, more than two triggering events may be required, such that expression of the expressible sequence is repressed only when all triggering events occur.

In embodiments, the sensor/reporter cassette comprises a NOR gate. In one embodiment, the presence of either (or both) of two conditions (i.e., triggering events) will repress expression of the expressible sequence. In one embodiment, more than two triggering events may be used, such that expression of the expressible sequence is repressed when one or more of the triggering events occur.

In embodiments, the sensor/reporter cassette comprises an OR gate. In one embodiment, the presence of either (or both) of two conditions (i.e., triggering events) will activate expression of the expressible sequence. In one embodiment, more than two triggering events may be used, such that expression of the expressible sequence is activated when one or more of the triggering events occur.

In embodiments, the sensor/reporter cassette comprises an XOR gate. In one embodiment, the presence of either of two conditions (i.e., triggering events), but not both, will activate expression of the expressible sequence. In one embodiment, more than two triggering events may be used, such that expression of the expressible sequence is activated when only one, only two, etc., but not all, of the triggering events occur.

In embodiments, the sensor/reporter cassette comprises an XNOR gate. In one embodiment, the presence of either of two conditions (i.e., triggering events), but not both, will repress expression of the expressible sequence. In one embodiment, more than two triggering events may be used, such that expression of the expressible sequence is repressed when only one, only two, etc., but not all, of the triggering events occur.

In some embodiments, the recombinant production reporter cell comprises one or more additional sensor/reporter cassettes, each expressing an additional protein that senses an additional triggering event. In some embodiments, the expressible sequence is only expressed when the additional triggering event(s) occur.

Provided herein are cell lines comprising a plurality of recombinant sensor cells as described herein.

FIG. 1 is a schematic of one embodiment of a recombinant production reporter cell as described herein. Protein 1 is expressed from a first sensor cassettes (not shown). Ligand 1 is a signal from a first triggering event. Upon binding of Ligand 1 to Protein 1, Protein 1 initiates a signal that results in binding of a transcriptional activator or transcriptional co-activator (or removal of a transcriptional repressor) at the promoter (P) of the logic cassette (iii). The logic cassette (iii) encodes a reporter gene that is expressed upon transcription from the promoter (P).

Although Protein 1 is depicted in FIG. 1 as membrane-bound proteins, one of skill in the art would understand that one or both proteins may be intracellular proteins, e.g. proteins that sense a signal from a triggering event indirectly (e.g., via a signal cascade through endogenous cell protein(s) that are activated by the triggering event) or directly (e.g., by binding a ligand from the signaling event, wherein the ligand is capable of active or passive diffusion into the cell).

For example, and without limitation, a recombinant production reporter cell as described herein may comprise a sensor cassette comprising a gene encoding a receptor operatively linked to a constitutive promoter, and a first logic cassette comprising a promoter that is activated only when activated ligand is present. When the recombinant production reporter cell is in an environment where ligand present, e.g., properly folded antibody, the reporter gene is expressed.

In some embodiments, the reporter cassette has a static set of reporter genes with a hybrid promoter that senses an analyte or ligand. The reporter cassette may have a static set of sequences in a prearranged organization. The reporter cassette may have any practical number of reporter genes. In this manner, staged production can be measured. For example, a single recombinant production reporter cell could report out each stage of production of a biological production system. One reporter such as GFP would be expressed when a constituent of stage 1 was sensed, another reporter such as mCherry would be expressed when a constituent of stage 2 was sensed, etc.

In embodiments, production workflow or stage of production could be reported either by having the recombinant reporter cell part of the production system if reporter cells are filtered out from the production system and/or imaged while part of the production system. Alternatively, the reporter cell could be contained in a membrane system that has access to an allowed inflow of analyte or ligand from the biological production system or through a slipstream pulled off the biological production system.

Sensed Environments

The sensed environment may be any environment of interest related to the production of a molecule of interest from a biological production system. In some embodiments, a first triggering event is present in a production cell microenvironment. In some embodiments, a first triggering event and a second triggering event are present in a biologic production cell microenvironment. In some embodiments, the first triggering event and/or the second triggering event is present in a microenvironment characterized by the presence of a properly folded antibody or molecule. In some embodiments, the biological product is produced by a prokaryotic system. In some embodiments, the biological product is produced by a eukaryotic system.

In some embodiments, the first triggering event is selected from cell density, cell stress, pH, hypoxia, heat, presence of a molecule of interest, or concentration of a molecule of interest. In some embodiments, the second triggering event is selected from cell density, cell stress, pH, hypoxia, heat, presence of a molecule of interest, or concentration of a molecule of interest. In some embodiments, the first triggering event or the second triggering event is the presence of intracellular components (properly folded antibodies, histones, ribosomal proteins, necrosis proteins, etc.) in the intercellular/extracellular environment. In some embodiments, the first or second triggering event is an event that stimulates growth of a cell (e.g., vascularization, presence of VEGF, etc.). In some embodiments, the first or second triggering event is an event that indicates apoptosis, cell stress, necrosis, or loss of cell adhesion.

In some embodiments, the molecule of interest is an antibody, cytokine, a chemokine, a metabolite, an exosome, an enzyme, a sugar, an intracellular component, a soluble checkpoint inhibitor, a signaling factor, a pathogen (e.g., a virus, a yeast cell, or a bacterial cell).

Triggering Events/Conditions and Recombinant Proteins

Molecules that indicate various triggering events are known in the art, as are proteins that sense those molecules. Non-limiting examples are provided in Table 1.

TABLE 1

Examples of triggering events, triggering molecules, and sensor proteins.

| Triggering Event | Triggering Molecule(s) | Sensor Protein(s) | References* |
|---|---|---|---|
| cell density | other cells in proximity | Hippo pathway, YAP, TAZ, GPCRs, e-cadherin | Sharif et al., Future Oncol. 2015 Dec.; 11(24): 3253-3260. |
| cytokines | cytokine (e.g., chemokines, interferons, interleukins, lymphokines, and tumour necrosis factors) | cytokine receptors | Bagley et al., Blood 1997 89:1471-1482. |
| chemokines | chemokines (e.g., CXC, CX3C, CC, or C chemokines) | chemokine receptors (e.g., CXC chemokine receptors, CC chemokine receptors, CX3C chemokine receptors and XC chemokine receptors) | Palomino and Marti, Einstein (Sao Paulo) 2015 Jul-Sep; 13(3): 469-473. |
| pH | proton (H+) | acid-sensing ion channels (ASICs) and proton-sensing GPCRs (e.g., GPR4, TDAG8, and OGR1) | Damaghi et al., Front. Physiol. 2013 Vol. 4, Article 370. |
| metabolites | metabolite (e.g., alcohol, amino acids, nucleotides, antioxidants, organic acids, polyols, vitamins, fatty acids, saccharides, lactate, ketone) | receptors (e.g., GPCRs) | Blad et al., Nature Reviews Drug Discovery volume 11, pages 603-619 (2012); Yuan et al., Mol Cell. 2013 Feb. 7; 49(3): 379-387. |
| exosomes and other extracellular vesicles | exosomes, microvesicles, ectosomes, microparticles, surface molecules | receptors | Tkach and Thery, Cell 164, Mar. 10, 2016, 1226-1232. |
| sugars | sugar or sugar moiety | lectins, sucrose transporters, glucosensors | Ghazarian, et al., Acta Histochem. 2011 May; 113(3): 236-247. |
| Soluble immune checkpoint markers | PD-L1 | PD1, CTLA4 | Manson et al., Annals of Oncology, Volume 27, Issue 7, 1 Jul. 2016, Pages 1199-1206. |
| angiogenic factors | VEGF, bFGF, TGF-α, TGF-β, platelet-derived endothelial growth factor, granulocyte colony-stimulating factor, placental growth factor, interleukin-8, hepatocyte growth factor, epidermal growth factor | receptors for each factor (e.g., VEGFR, TGFR, EGFR, IL receptors, etc.) | Nishida et al., Vasc Health Risk Manag. 2006 Sep.; 2(3): 213-219. |
| tumor-specific factors | neoepitopes; tumor-associated antigens | antibodies, CARs | WO2017205810; WO2017066256; WO2018089637 |
| apoptosis | apoptosis-associated factors (e.g., cleaved cytokeratin-18 (c-CK18), cleaved caspase-3 (c-cas-3), cleaved lamin A (c-lam-A), phosphorylated | receptors, antibodies | Ward et al., British Journal of Cancer volume 99, pages 841-846 (16 Sep. 2008) |

TABLE 1-continued

Examples of triggering events, triggering molecules, and sensor proteins.

| Triggering Event | Triggering Molecule(s) | Sensor Protein(s) | References* |
|---|---|---|---|
| | histone H2AX (gammaH2AX), cleaved poly(ADP ribose) polymerase (c-PARP), phosphatidylserine, Cytokeratins, Nucleosomal DNA, Apo-1/Fas, Fas ligand (sFasL), Bcl-2/Bcl-xl/Mcl-1, p53, phospo-p53, p21 wafi, pH2AX, cytochrome c, Activated caspases 2, 3, 7, 8 and 9, fortilin) | | |
| stress | stress proteins, cytokines, chemokines, apoptotic factors, etc. | receptors, etc. | Milisav (2011). Cellular Stress Responses, Adv. in Regen. Med., S. Wislet-Gendebien (Ed.) |
| loss of adhesion | cell adhesion molecules (CAMs, e.g., integrins, immunoglobulin (Ig) superfamily, cadherins, and selectins) | CAMs | |
| pathogens | pathogen (bacterial cell, fungus, virus, parasite, etc) or an antigen or toxin therefrom | receptors (e.g., TLRs), antibodies, lectins, | Akira et al. Cell 124, 783-801, Feb. 24, 2006. |
| hypoxia | intracellular oxygen levels | HIFα, HIFβ, heme protein, prolyl hydroxylase | Zhu and Bunn, Science. 2001 Apr. 20; 292(5516): 449-451. |
| heat/temperature | heat | vanilloid receptor | U.S. Pat. No. 7,396,910; Moqrich et al., Science 04 Mar. 2005: Vol. 307, Issue 5714, pp. 1468-1472 |

*Each reference is incorporated herein by reference in its entirety.

In some embodiments, the proteins that sense a ligand and/or activate expression are fusion proteins, for example having a sensor (e.g., ligand-biding) domain from one protein and an effector domain (e.g., activator domain or repressor domain) from a different protein. In some embodiments, the same protein senses (e.g., binds) the ligand and activates or represses transcription, e.g., of the expressible sequence. In some embodiments, the sensor protein modulates activity of another protein that in turn modulates transcription, e.g., of the expressible sequence. The protein that is modulated by the sensor protein may be an endogenous protein, or it may be a recombinant protein.

In some embodiments, the sensor protein is a chimeric antigen receptor (CAR) or similar to a CAR. That is, the ligand-binding domain of the sensor comprises an antibody (or fragment thereof) capable of binding to the ligand, and the effector domain comprises a signaling molecule that results in repression or activation of the expressible sequence upon binding of the ligand to the antibody (or fragment thereof).

Of course, it should be recognized that a ligand may be a molecule as indicated above, or may be a down-stream effector of such a molecule.

Expressible Sequences

In embodiments, the expressible sequence encodes a reporter. In some embodiments, the reporter may be any reporter protein or RNA that can be detected in vivo, ex vivo, or in vitro. In some embodiments, the reporter is selected from a fluorescent protein, a cell surface marker, a detectable RNA molecule, a detectable DNA molecule, a luciferase, or a reporter enzyme. Such reporters are well known in the art. In some embodiments, the reporter can be detected by imaging the cell. In some embodiments, the reporter can be detected in a sample from the production system.

In some embodiments, the expressible sequence encodes a binding peptide linked to a reporter. For example, an antibody, ligand for a protein of interest (e.g., a cell surface protein expressed by a tumor cell), or other binding peptide may be linked to (fused with) a reporter such as a fluorescent protein. In some embodiments, the binding peptide recognizes (binds to) an epitope that is present in a particular microenvironment (e.g., tumor microenvironment). In some embodiments, expression of the binding peptide linked to a reporter allows visualization of a particular environment or cell. In some embodiments, the antibody is a single domain antibody (e.g., camelid antibody) or epitope-binding fragment thereof. Single domain antibodies are known in the art, for example as described in Harmsen and Haard, which is incorporated herein by reference in its entirety.

In some embodiments, the reporter that can be viewed by eye under certain conditions (e.g., a fluorescent reporter).

In some embodiments, the reporter is selected from a fluorescent protein, a cell surface marker, a detectable RNA molecule, a detectable DNA molecule, a luciferase, or a reporter enzyme. In some embodiments, the fluorescent protein is selected from gfp, mcherry, bfp, iRFP, mRuby, dsRed, EGFP, citrin, mOrange, TagBFP, mTurquoise, cerulean, bilirubin inducible fluorescent protein, flavin based fluorescent protein (FbFP), small ultra-red fluorescent protein. In some embodiments, the bilirubin inducible fluorescent protein is selected from UnaG, dsRed, eqFP611, Dronpa, TagRFP, KFP, EosFP, Dendra, IrisFP.

Vectors

Any type of vector may be used, including, without limitation, viruses, plasmids, and the like. In some embodiments, the nucleic acids (e.g., the first, second and/or third nucleic acids) are present on one or more vectors in the cell. In some embodiments, one, two, three or more of the nucleic acids is present in a single vector.

In an aspect, provided herein are recombinant vectors comprising one or more of a sensor cassette and a reporter cassette. The sensor cassette includes a first recombinant nucleic acid sequence encoding a sensor protein having a ligand binding portion and an activator portion, where the ligand binding portion is capable of binding a ligand from a triggering event related to the at least one constituent. The reporter cassette includes a second recombinant nucleic acid sequence comprising a promoter sequence operably linked to an expressible reporter sequence encoding a reporter protein, where expression from the promoter sequence is activated by the activator portion of the sensor protein, such that the expressible sequence is expressed only after the triggering event occurs.

Type of Cells

In embodiments, the recombinant production reporter cell is bacteria, virus, fungus, yeast, parasite, tumor cell, plant cell, cell line, or an immune cell. In some embodiments, the cell line is a CHO cell, a CAR-CHO cell, or an EC7 cell. In some embodiments, the immune cell is an immunocompetent cell. In some embodiments, the immune cell is a B cell, dendritic cell, natural killer cell, an invariant natural killer T cell (INKT), a T cell, or a CAR-T cell.

In some embodiments, the recombinant production reporter cell is an enucleated cell that is capable of transcription and translation. In some embodiments, the recombinant production reporter cell is an exosome that is capable of transcription and translation.

In some embodiments, the production system is a production system for a therapeutic cell, and the recombinant production reporter cell is the same type of cell as the therapeutic cell (e.g., CAR T cell). In some embodiments, the production system is a production system for a therapeutic cell, and the recombinant production reporter cell is a different type of cell.

In embodiments, the recombinant sensor cell is fixed on a solid support, embedded in a gel, part of a matrix, or fixed within a dialysis membrane. In embodiments, the recombinant sensor cell is fixed on a solid support. In embodiments, the recombinant sensor cell is embedded in a gel. In embodiments, the recombinant sensor cell is part of a matrix. In embodiments, the recombinant sensor cell is fixed within a dialysis membrane The present disclosure also relates, in part, to methods of making recombinant sensor cells as described herein. Methods of inserting recombinant nucleic acids into cells are known in the art e.g. Green and J. Sambrook.

In embodiments, provided are methods for producing a recombinant production reporter cell as described herein. The methods include introducing a sensor cassette and a reporter cassette into a cell. The sensor cassette includes a first recombinant nucleic acid sequence encoding a sensor protein having a ligand binding portion and an activator portion, and the reporter cassette includes a second recombinant nucleic acid sequence comprising a promoter sequence operably linked to an expressible reporter sequence encoding a reporter protein.

In some embodiments, the nucleic acids are introduced into the cell by transient transfection. In some embodiments, the nucleic acids are stably transfected into the cell.

Methods of Using Recombinant Reporter Cells

A recombinant production reporter cell as described herein may be engineered for quality control protocols for a biological production system, e.g. production of a biological therapeutic. For example, recombinant production reporter cell may be used to detect at least one constituent in a biological production system. The method of detecting the at least one constituent includes contacting the biological production system with a recombinant reporter cell and detecting a reporter protein. The reporter cell is capable of sensing the constituent by binding a ligand from a triggering event related to the at least one constituent. The interaction between the triggering event and the reporter cell sensing the ligand leads to expression of a reported that can be detected. For example, the triggering event may be a molecule, e.g., a protein that is expected to be present in the biological production system. Thereby, the method provides detecting the at least one constituent relative to the sample from the biological production system.

In an aspect, the biological production system includes bacteria, virus, fungus, yeast, parasite, tumor cell, plant cell, or an immune cell. For example, a recombinant production reporter cell as described herein may be used to detect at least one constituent in a biological production system. The biological production system could be CAR-T production, vaccine production, blood derivative production, blood component production, allergenic extract production, xenotransplantation product production, or gene therapy production.

By way of another non-limiting example, the production system may be production of a CAR-T cell and a recombinant production reporter cell as described herein can be used to detect whether a CAR-T cell has been produced properly by determining whether one or more particular constituents is present in the biological production microenvironment. CAR-T production encompasses T-cell source collection and processing followed by CAR-T cell preparation CAR-T cell preparation involves T-cell selection and/or activation, genetic modification with a CAR cDNA followed by large-scale expansion, and end-of-process formulation. Production stages of CAR-T cells include virus generation, T-cell separation, T-cell modification, and Car-T cell amplification. During any of these stages, a recombinant production reporter cell as described herein may be used to detect a triggering event. For example, the triggering event may be a molecule, e.g., a protein or analyte, a particular tumor-associated antigen binding sequence or a neoepitope that is expected to be present at a particular stage of production of the CAR-T cell. Alternatively, the recombinant production reporter cell as described herein may be used to detect contamination of a stage of CAR-T cell production (e.g., by a bacteria, yeast, or virus).

In an embodiment, the recombinant production reporter cell as described herein may be used to detect contamination of a biological production system by a non-homologous cell. For example, where multiple patient-derived cells are processed in parallel, the recombinant production reporter cell may detect the presence of a cell from a different patient. In another embodiment, the recombinant production reporter cell as described herein may be used to detect improper antigen receptor products.

By way of another non-limiting example, the recombinant production reporter cell as described herein may be used to detect a stage of vaccine production. Vaccine production can be generally divided into five stages: 1) generation of the antigen, 2) release and isolation of the antigen, 3) purification, 4) addition of other components, and 5) packaging. During any of these stages, a recombinant production reporter cell as described herein may be used to detect a triggering event. For example, the triggering event may be a molecule, e.g., a protein or analyte, a target antigen, or an epitope that is expected to be present at a particular stage of production of the vaccine production. Alternatively, the recombinant production reporter cell as described herein may be used to detect contamination of a stage of vaccine production (e.g., by a bacteria, yeast, or virus).

By way of another non-limiting example, the recombinant production reporter cell as described herein may be used to detect a stage of xenotransplantation product production. Xenotransplantation is any procedure that involves the transplantation, implantation or infusion into a human recipient of either (a) live cells, tissues, or organs from a nonhuman animal source, or (b) human body fluids, cells, tissues or organs that have had ex vivo contact with live nonhuman animal cells, tissues or organs. Such products harbor a risk of co-administering an infectious agent. Therefore, monitoring production requires monitoring presence of infectious disease agents such as viruses and/or bacteria. During any of the stages of xenotransplantation product production, a recombinant production reporter cell as described herein may be used to detect a triggering event. For example, the triggering event may be a molecule, e.g., a protein or analyte, a target antigen, or an epitope that is expected to be present at a particular stage of production of the vaccine production. Alternatively, the recombinant production reporter cell as described herein may be used to detect contamination of a stage of vaccine production (e.g., by a bacteria, yeast, or virus).

Kits

In some embodiments, a kit is provided that includes at least one of: a) a sensor cassette comprising a first recombinant nucleic acid sequence encoding a plurality of sensor proteins, each sensor protein having a ligand binding portion and an activator portion, wherein the ligand binding portion of each distinct sensor protein is capable of binding a distinct ligand from a distinct triggering event; and b) a reporter cassette comprising a second recombinant nucleic acid sequence comprising a plurality of distinct promoter sequences, each promoter operably linked to a distinct expressible sequence, wherein expression from each promoter sequence is activated by the activator portion of a respective distinct sensor protein, such that the expressible sequence is expressed only after a distinct triggering event occurs.

In some embodiments, the kit comprises at least two of the first sensor cassette, second sensor cassette, and/or the first logic cassette.

In some embodiments, the first sensor cassette, second sensor cassette, and the first logic cassette are present in a single vector. In some embodiments, the first sensor cassette, second sensor cassette, and/or the first logic cassette are present in two or more separate vectors.

In some embodiments, the kit further comprises a cell (or plurality of cells) to be transfected/infected with the nucleic acid sequences/vector(s).

Another aspect of the inventive subject matter includes production apparatus that can leverage the disclosed recombinant reporter cells. For example, a production apparatus can comprise a computer controlled assembly including a non-transitory computer readable memory (e.g., RAM, flash, HDD, SSD, etc.) and one or more processors. The memory stores software instructions that cause the processors to control the overall assembly. The assembly can comprise one or more a production chamber where the target biologics are produced and one or more sensors that observe the production chamber. An example production apparatus that can be adapted for use with the inventive subject matter is a "GMP in a box" device described in international patent application publication WO 2018/052991 to Armani et al. titled "Systems, Apparatus, and Methods for Controlling a Movement of a Cell Culture to Optimize Cell Growth" filed Sep. 13, 2017, which is incorporated herein by reference in its entirety. The advantage of using such a device is twofold. First it is programmable with a desired behavior. Second, it includes a microscope (e.g., one or more sensors, etc.) that is able to observe the production chamber in real-time.

Consider a use-case where production of a biologic (e.g., an NK cell therapy, a CAR-T therapy, etc.) via the above GMP-in-a-box device and comprises a complex manufacturing protocol. Recombinant reporter cells can be constructed that report on each stage of production, for example reporting a first stage of production using GFP and a second stage of production using mCherry, and so on. During production the sensor, a camera in this use-case, observes the reported amount of the reporter proteins as a function of time. The processor can compare the observed state of production (e.g., stage of production, presence of absence of a constituent) to an expected signature (e.g., a digital profile, etc.) to determine if production is on track. If not, the processor can cause the assembly to take appropriate action. For example, if there should be a uniform distribution of GFP and mCherry in the culture according to the expected signature, but there is not due to clumping the processor can cause the assembly to shake the production chamber to ensure compliance with the expected production signature. This approach can be achieved using image processing techniques such as those available via the open source computer vision package OpenCV (e.g., www.opencv.org).

Still further, in some embodiments, the recombinant reporter cell can be configure with a "kill" switch once production reaches a desired state (e.g., stage of production, presence or absence of a constituent, etc.). The kill switch can cause apoptosis or otherwise change the nature of the recombinant report cell so that it can be filtered from the production culture. Returning to the GMP-in-a-box example, the production chamber can be instrumented with an in-line flow filter by which reporter cells can be shunted or filtered out, possibly via one or more flow cytometry techniques.

Example

In the following examples, the sensor cassette used in 293T cells was a TGF-beta receptor that was encoded on the genome of the 293T cell. Of course, it should be appreciated that the sensor cassette could have also been located on a recombinant plasmid transfected into the cell or recombinant nucleic acid integrated into the genome of the cell. The reporter cassette in the present examples comprised a sequence portion encoding a chimeric protein under the control of the TGF-beta response element as shown in more detail further below. To assess the function of the reporter cassette, the firefly luciferase gene was stably integrated into the genome of the 293T by transfecting the commercially available plasmid pGL4.48 (Promega) using Lipofectamine 2000 (Invitrogen) and selecting with hygromycin (10 µg/ml).

Figure 2:
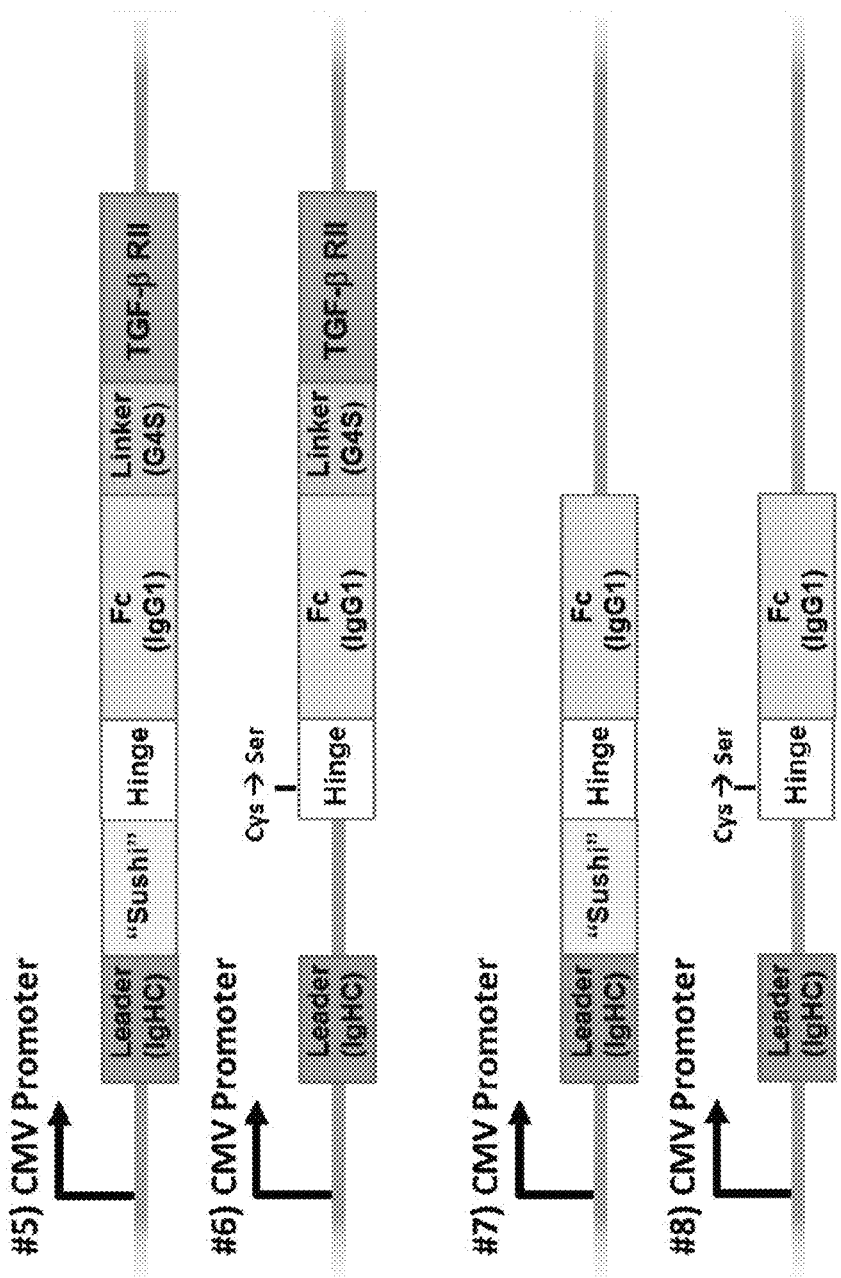
FIG. 2 is a schematic illustration of recombinant nucleic acids as described herein. All constructs shown herein express constitutively.

As controls for the function of the chimeric protein, various constructs were prepared as is schematically shown in FIG. 2. Here, all constructs were constitutively expressed from a CMV promotor. Two chimeric proteins were constructed that included a TGF-beta trap portion to bind extracellular soluble TGF-beta (upper two constructs in FIG. 2), while two further corresponding constructs lacked the TGF-beta trap portion (upper two constructs in FIG. 2). Further differences in the construct were in the use of the Sushi domain and Hinge domain as is shown in FIG. 2.

Figure 3:
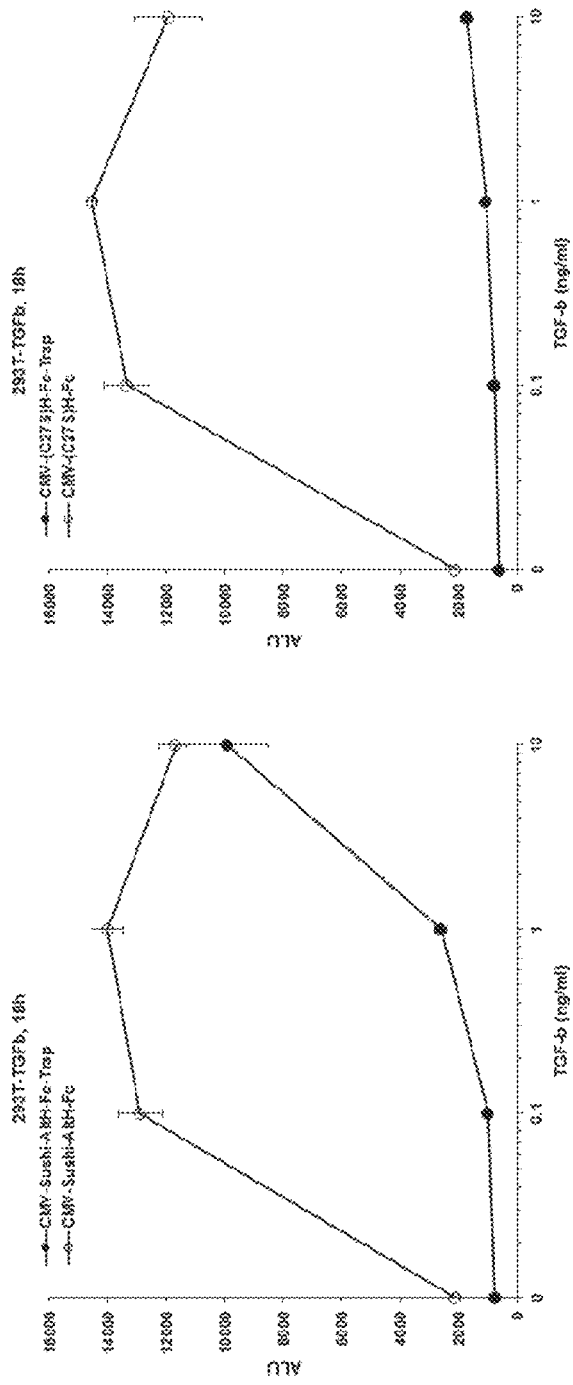
FIG. 3 depicts exemplary results using the recombinant nucleic acid of FIG. 2 herein.

Results for these constructs in 293T cells are shown in FIG. 3. Here, 293T cell lines stably expressing TGF-beta induced luciferase were transfected with CMV-driven expression constructs as shown in FIG. 2 comparing the Sushi domain (Sushi), Altor hinge (AltH) Fc domain (Fc) with or without the TGFBRII (Trap) vs. the modified hinge ((C27S)H), Fc with or without the TGFBRII (Trap). Cells were incubated overnight, washed and stimulated with TGF-b at the indicated concentrations. The resulting luciferase activity was measured after 18 hours using Luciferase Assay System (Promega) according to the manufacturer's recommendation. The results in FIG. 3 show that the trap constructs were capable of inhibiting TGF-b at low levels (0-1 ng/ml), with the modified construct being more effective at high concentrations.

Figure 4:
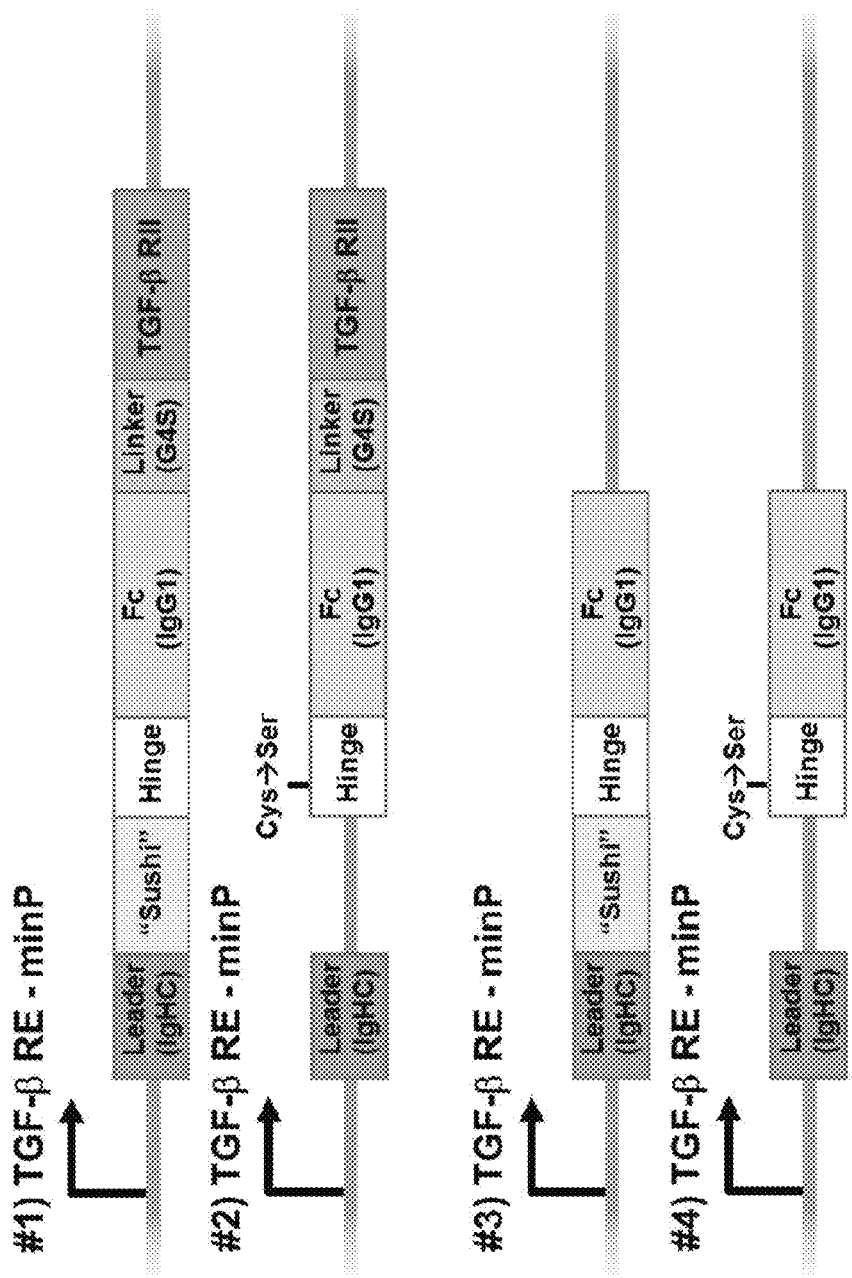
FIG. 4 is a schematic illustration of other recombinant nucleic acids as described herein. All constructs shown herein express inducibly in response to TGF-β.
Figure 5:
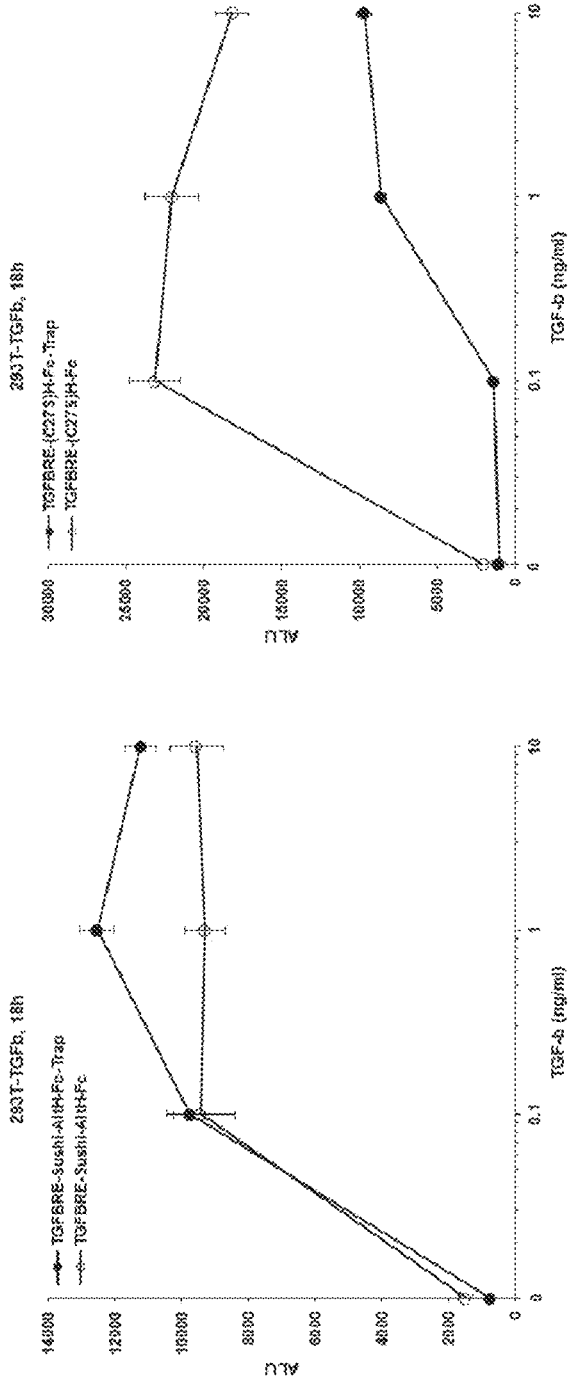
FIG. 5 depicts exemplary results using the recombinant nucleic acid of FIG. 4.

Similarly, constructs of inducibly expressed TGF beta traps and control constructs are shown in FIG. 4 where expression of the constructs was induced from the TGF-beta response element minimum promotor. Here, 293T cell lines stably expressing TGF-beta induced luciferase were transfected with TGF-b response element (TGFBRE)-driven expression constructs as shown in FIG. 4 comparing the Sushi domain (Sushi), Altor hinge (AltH) Fc domain (Fc) with or without the TGFBRII (Trap) vs. the modified hinge ((C27S)H), Fc with or without the TGFBRII (Trap). Cells were incubated overnight, washed and stimulated with TGF-beta at the indicated concentrations. The resulting luciferase activity was measured after 18 hours. The data in FIG. 5 show that original construct was less able to block TGF-b activity in the inducible format, whereas the modified construct was effective at low concentrations (0.1 ng/ml), and still demonstrated neutralizing activity at mid to high concentrations (1-10 ng/ml).

Viewed from a different perspective, it should thus be appreciated that recombinant cells can be prepared that contain a sensor cassette that is sensitive to a desired ligand, and that once binding of the ligand (here TGF-beta) occurred, expression of a reporter gene in a reporter cassette can be activated via the sensor protein to produce a detectable and quantifiable event. In the above example, the sensor cassette could be located on the genome (here: genomic sequence that encodes the TGF-beta receptor) while the reporter cassette is encoded on an extragenomic nucleic acid that includes a TGF-beta responsive promoter (here: TGF-beta response element minimum promoter) that controls expression of a desired reporter or effector gene (here: TGF-beta trap). In this example, to help quantitate the expression of the desired reporter or effector gene, the cells also included a recombinant sequence that encoded a luciferase gene under the control of a TGF-beta response element.

All publications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

What is claimed is:

1. A method of detecting at least one constituent in a biological production system, the method comprising:
   (i) contacting a sample from the biological production system with a recombinant sensor cell comprising:
      a) a sensor cassette comprising a first recombinant nucleic acid sequence encoding TGF-beta induce luciferase, a sushi domain, an altor hinge domain, a Fc domain, and a TGFBRII trap domain;
      b) a reporter cassette comprising a second recombinant nucleic acid encoding TGF-beta response element, a sushi domain, an altor hinge domain, a Fc domain, a TGFBRII trap, and a CMV promoter sequence;
   (ii) detecting expression of TGF-beta protein, thereby detecting the at least one constituent relative to the sample from the biological production system;
   wherein the at least one constituent is TGF-beta, and wherein the recombinant sensor cell is a 293T cell.

2. The method of claim 1, wherein
   a) the first recombinant nucleic acid sequence encodes a plurality of sensor proteins, each sensor protein having a ligand binding portion and an activator portion, wherein the ligand binding portion of each distinct sensor protein is capable of binding a distinct ligand from a distinct triggering event; and
   b) wherein the second recombinant nucleic acid sequence comprises a plurality of distinct promoter sequences, each promoter operably linked to a distinct expressible sequence, wherein expression from each promoter sequence is activated by the activator portion of a respective distinct sensor protein, and wherein the expressible sequence is expressed only after a distinct triggering event occurs, and wherein each expressible sequence encodes a reporter.

3. The method of claim 2, wherein the triggering event corresponds to a stage of production of the molecule or of the cell of interest.

4. The method of claim 2, wherein each triggering event is independently selected from cell density, pH, hypoxia, presence of a cell of interest, presence of a molecule of interest, or concentration of a molecule of interest.

5. The method of claim 1, wherein the sample from the biological production system comprises a cell.

6. The method of claim 5, wherein the cell is selected from bacteria, virus, fungus, yeast, parasite, tumor cell, plant cell, cell lines, or an immune cell.

7. The method of claim 6, wherein the immune cell is selected from a B cell, dendritic cell, natural killer cell, an invariant natural killer T cell (iNKT), a T cell, or a CAR-T cell.

8. The method of claim 1, wherein the production system is a CAR-T cell manufacturing system and the molecule of interest is a secreted cytokine.

9. The method of claim 1, wherein the recombinant sensor cell is fixed on a solid support.

10. The method of claim 1, wherein the at least one constituent is unique to a stage of production of the system, wherein the stage is selected from virus generation, T-cell separation, T-cell modification, and CAR-T cell amplification.

11. The method of claim 1, wherein the at least one constituent is unique to a stage of production of the system, and wherein the stage is selected from acquisition of a cell; genetic editing of a cell; transfection, transduction, or infection of a cell; thawing of a population of cells; freezing of a population of cells; cell culture or expansion; harvesting of the cell of interest or the molecule of interest; or packaging of the cell of interest or the molecule of interest.

* * * * *